(12) United States Patent
Sadler et al.

(10) Patent No.: US 8,329,028 B2
(45) Date of Patent: Dec. 11, 2012

(54) SOLID CATALYST HYDROCARBON CONVERSION PROCESS USING STACKED MOVING BED REACTORS

(75) Inventors: Clayton C. Sadler, Arlington Heights, IL (US); Mary Jo Wier, Schaumburg, IL (US); Laurence O. Stine, Western Springs, IL (US); Christopher Naunheimer, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 252 days.

(21) Appl. No.: 12/958,818

(22) Filed: Dec. 2, 2010

(65) Prior Publication Data

US 2011/0152591 A1 Jun. 23, 2011

Related U.S. Application Data

(60) Provisional application No. 61/287,287, filed on Dec. 17, 2009.

(51) Int. Cl.
*C10G 65/12* (2006.01)
*C10G 47/00* (2006.01)
*C10G 47/28* (2006.01)
(52) U.S. Cl. ............ 208/59; 208/108; 208/176
(58) Field of Classification Search .......... 208/59, 208/108, 176
See application file for complete search history.

(56) References Cited

U.S. PATENT DOCUMENTS

| 3,838,038 | A | 9/1974 | Greenwood et al. |
| 4,069,134 | A | 1/1978 | Greenwood et al. |
| 5,849,976 | A | 12/1998 | Gosling et al. |
| 7,622,620 | B2 | 11/2009 | Peters et al. |
| 7,794,585 | B2 | 9/2010 | Leonard et al. |
| 2006/0213811 | A1 | 9/2006 | Clay et al. |

FOREIGN PATENT DOCUMENTS

WO  97 26313 A1  7/1997

OTHER PUBLICATIONS

Schmitz, "Deep Desulfurization of Diesel Oil Kinetic Studies and Process-Improvement by the Use of a Two-Phase Reactor with Pre-Saturator", Chemical Engineering Science, 2004, pp. 2821-2829, vol. 59.

*Primary Examiner* — Randy Boyer
(74) *Attorney, Agent, or Firm* — Maryann Maas

(57) ABSTRACT

Systems and processes for hydrocarbon conversion are provided that utilize a plurality of moving bed reactors. The reactors may be moving bed radial flow reactors. Optional mixers that mix a portion of a second hydrocarbon feed with the effluent stream from an upstream reactor, to produce reactor feed streams may be employed, and the reactor feed streams may be introduced at injection points prior to each reactor. Catalyst can be provided from the reaction zone of one reactor to the reaction zone of a downstream reactor through catalyst transfer pipes, and can be regenerated after passing through the reaction zones of the reactors. The moving bed reactors can be stacked in one or more reactor stacks.

21 Claims, 3 Drawing Sheets

SOLID CATALYST HYDROCARBON CONVERSION PROCESS USING STACKED MOVING BED REACTORS

CROSS REFERENCE TO RELATED APPLICATION

This application claims the benefit of priority of U.S. Provisional Application 61/287,287, filed Dec. 17, 2009, the contents of which are hereby incorporated by reference in its entirety.

FIELD OF THE INVENTION

The systems and processes described herein relate to liquid phase hydrocarbon conversion processes utilizing a solid catalyst in a moving bed mode. The moving bed mode may be radial flow moving beds. The systems and processes described herein can be utilized, for example, for alkylation of hydrocarbons such as aromatics or paraffins to produce useful chemicals and motor fuel.

BACKGROUND OF THE INVENTION

The invention may be applied to a variety of different hydrocarbon conversion reactions. Some of these reactions may be described in simple terms such as A+B→C+D; or E→F; or G→H+I; or J+K→L. Additional reactants may be used or additional products may be generated depending upon the specific reaction. However, to benefit from the present invention, the reactions are being conducted in the liquid phase and are catalyzed by a solid catalyst operated in the moving bed mode. At least one reactant is continuously introduced to the moving bed of catalyst containing a sufficient amount of catalyst effective to catalyze the reaction. The reactant(s) are in the liquid phase, and the reactant(s) may be present in a mixture with a liquid fluid carrier. The moving bed of catalyst is operated at conditions optimal to the desired reaction. As the reactant(s) contacts the catalyst, the hydrocarbon conversion reaction occurs to form at least one product. When chemical equilibrium is reached, the ratio of the concentrations of the reactants and products remain constant, and no increase in the concentrations of product(s) are accomplished. If the hydrocarbon conversion reaction is not equilibrium limited, the reaction may continue to a desired endpoint. The process is continuous, with reactant continuously being introduced, product being continually removed, and the catalyst bed continuously moving.

Numerous variations of this simple illustration will be apparent to one skilled in the art. For example, one would understand how to apply this invention to liquid phase hydrocarbon conversion processes such as cracking, hydrocracking, alkylation of aromatics, alkylation of isoparaffins, isomerization, polymerization, reforming, dewaxing, hydrogenation, dehydrogenation, transalkylation, dealkylation, hydration, dehydration, hydrotreating, hydrodenitrogenation, hydrodesulfurization, ring opening, and hydroprocessing processes.

For ease of understanding, the details of the invention will be discussed herein in terms of an alkylation reaction, which is the reaction between a feed hydrocarbon and an alkylating agent. Hydrocarbon alkylation is widely used in the petroleum refining and petrochemical industries to produce a variety of useful acyclic and cyclic hydrocarbon products used as motor fuel, plastic and detergent precursors and petrochemical feedstocks.

In the production of motor fuels, the feed hydrocarbon is typically isobutane (I) and the alkylating agent is typically olefin (O). It is preferred to operate with an excess of isobutane in compared to olefin in order to promote the preferred alkylation reaction (I+O=Alkylate) instead of the undesirable oligomerization reaction (O+O=oligomer).

For example, large amounts of high octane gasoline are produced commercially by alkylation of isobutane with butenes or propylene. This significantly increases the value of the C4 feed hydrocarbons. Additionally, large amounts of valuable alkyl aromatic hydrocarbons including cumene, ethylbenzene and C10 to C15 linear alkylaromatics are produced by the alkylation of benzene with olefins of the appropriate carbon number.

Historically, liquid-acid alkylation processes have been used commercially, and such processes commonly employ hydrofluoric acid (HF) or sulfuric acid (H2SO4) as catalysts. Environmental and safety concerns, among other factors, have led to the development of alkylation processes utilizing solid catalysts. However, solid alkylation catalysts tend to have relatively quick deactivation times (e.g., about 2-24 hours) and require frequent regeneration.

Known liquid acid alkylating processes are typically designed with external isobutane to olefin ratios (I/O) between 5/1 and 15/1. External I/O is defined as total isobutane to the reaction section divided by the total feed olefin. It is desirable to have a solid catalyst alkylation process with the same range of external I/O ratios to remain cost competitive to liquid acid alkylation. The I/O ratio can be increased further inside the reactor section by recycling isobutane. This Internal I/O is defined as the local isobutane to local olefin concentration. The internal I/O ratio can also be increased by dividing the olefin feed into multiple injections, and requires mixing to ensure the feed olefin is completed dispersed in the reaction liquid stream. For solid catalyst alkylation, higher internal I/O ratios will result in longer catalyst lives and an improved product quality, but will also increase the capital and operating costs of the process.

With respect to solid catalyst alkylation, moving bed solid catalyst alkylation processes have a number of advantages over fixed bed solid catalyst alkylation processes, as described, for example, in U.S. Pat. No. 5,849,976 to Gosling, et al. at Col 2, lines 66-67 and Col 3, lines 1-9, which explains that the use of moving bed reactors has the advantage of reducing both the catalyst and liquid hydrocarbon inventory in the plant, which are desirable cost and safety benefits, and also that use of moving beds can function to transfer the catalyst between reaction and regeneration zones, which has the benefit of allowing the catalyst to be partially or totally replaced without disrupting the operation of the process. The U.S. Pat. No. 5,849,976 describes, for example, the utilization of slowly moving cylindrical beds of solid catalyst in a process featuring a cooling zone within the reaction zone and a moving bed catalyst regeneration zone. U.S. Pat. No. 5,849,976 at Abstract. Additionally, U.S. Pat. No. 3,838,038 to Greenwood et al. describes a method of operating a continuous hydrocarbon process employing solid catalyst particles that includes a moving bed reaction zone and a continuous regeneration zone. U.S. Pat. No. 3,838,038 at Col. 2 lines 25-30.

Another specific hydrocarbon conversion process likely to benefit from this invention is hydroprocessing.

Petroleum refiners often produce desirable products such as turbine fuel, diesel fuel, middle distillates, naphtha, and gasoline boiling hydrocarbons among others by hydroprocessing a hydrocarbon feed stock derived from crude oil or heavy fractions thereof. Hydroprocessing can include, for example, hydrocracking, hydrotreating, hydrodesulfurization and the like. Feed stocks subjected to hydroprocessing can be vacuum gas oils, heavy gas oils, and other hydrocarbon streams recovered from crude oil by distillation. For example, a typical heavy gas oil comprises a substantial portion of hydrocarbon components boiling above about 371° C. (700° F.) and usually at least about 50 percent by weight boiling above 371° C. (700° F.), and a typical vacuum gas oil normally has a boiling point range between about 315° C. (600° F.) and about 565° C. (1050° F.).

Hydroprocessing is a process that uses a hydrogen-containing gas with suitable catalyst(s) for a particular application. In many instances, hydroprocessing is generally accomplished by contacting the selected feed stock in a reaction vessel or zone with the suitable catalyst under conditions of elevated temperature and pressure in the presence of hydrogen as a separate phase in a three-phase system (gas/liquid/solid catalyst). Such hydroprocessing is commonly undertaken in a trickle-bed reactor where the continuous phase is gaseous and not liquid.

In the trickle bed reactor, an excess of the hydrogen gas is present in the continuous gaseous phase. In many instances, a typical trickle-bed hydroprocessing reactor requires up to about 1778 nm$^3$/m$^3$ (10,000 SCF/B) of hydrogen at pressures up to 17.3 MPa (2500 psig) to effect the desired reactions. However, even though the trickle bed reactor has a continuous gaseous phase due to the excess hydrogen gas, it is believed that the primary reactions are taking place in the liquid-phase in contact with the catalyst, such as in the liquid filled catalyst pores. As a result, for the hydrogen gas to get to the active sites on the catalyst, the hydrogen must first diffuse from the gas phase into the liquid-phase and then through the liquid to the reaction site adjacent the catalyst.

While not intending to be limited by theory, under some hydroprocessing conditions the hydrogen supply available at the catalytic reaction site may be a rate limiting factor in the hydroprocessing conversions. For example, hydrocarbon feed stocks can include mixtures of components having greatly differing reactivities. While it may be desired, for example, to reduced the nitrogen content of a vacuum gas oil to very low levels prior to introducing it as a feed to a hydrocracking reactor, the sulfur containing compounds of the vacuum gas oil will also undergo conversion to hydrogen sulfide. Many of the sulfur containing compounds tend to react very rapidly at the operating conditions required to reduce the nitrogen content to the desired levels for hydrocracking. The rapid reaction rate of the sulfur compounds to hydrogen sulfide will tend to consume hydrogen that is available within the catalyst pore structure thus limiting the amount of hydrogen available for other desired reactions, such as denitrogenation. This phenomenon is most acute within the initial portions (i.e., about 50 to about 75 percent) of the reaction zones. Under such circumstances with the rapid reaction rate of sulfur compounds, for example, it is believed that the amount of hydrogen available at the active catalyst sites can be limited by the diffusion of the hydrogen through the feed (especially at the initial portions of the reactor). In these circumstances, if the diffusion of hydrogen through the liquid to the catalyst surface is slower than the kinetic rates of reaction, the overall reaction rate of the desired reactions (i.e., denitrogenation, for example) may be limited by the hydrogen supply and diffusion. In one effort to overcome the limitations posed by this phenomenon (hydrogen depletion), hydroprocessing catalysts can be manufactured in small shapes such as tri-lobes and quadric-lobes where the dimension of the lobe may be on the order of 1/30 inch. However, such small catalyst dimensions also can have the shortcoming of creating larger pressure drops in the reactor due to the more tightly packed catalyst beds.

Two-phase hydroprocessing (i.e., a liquid hydrocarbon stream and solid catalyst) has been proposed to convert certain hydrocarbon streams into more valuable hydrocarbon streams in some cases. For example, the reduction of sulfur in certain hydrocarbon streams may employ a two-phase reactor with pre-saturation of hydrogen rather than using a traditional three-phase system. See, e.g., Schmitz, C. et al., "Deep Desulfurization of Diesel Oil: Kinetic Studies and Process-Improvement by the Use of a Two-Phase Reactor with Pre-Saturator," Chem. Eng. Sci., 59:2821-2829 (2004). These two-phase systems only use enough hydrogen to saturate the liquid-phase in the reactor. As a result, the reactor systems of Schmitz et al. have the shortcoming that as the reaction proceeds and hydrogen is consumed, the reaction rate decreases due to the depletion of the dissolved hydrogen. As a result, such two-phase systems as disclosed in Schmitz et al. are limited in practical application and in maximum conversion rates.

Other uses of liquid-phase reactors to process certain hydrocarbonaceous streams require the use of diluent/solvent streams to aid in the solubility of hydrogen in the unconverted oil feed and require limits on the amount of gaseous hydrogen in the liquid-phase reactors. For example, liquid-phase hydrotreating of a diesel fuel has been proposed, but requires a recycle of hydrotreated diesel as a diluent blended into the oil feed prior to the liquid-phase reactor. In another example, liquid-phase hydrocracking of vacuum gas oil is proposed, but likewise requires the recycle of hydrocracked product into the feed to the liquid-phase hydrocracker as a diluent. In each system, dilution of the feed to the liquid-phase reactors is required in order to effect the desired reactions. Because hydrotreating and hydrocracking typically require large amounts of hydrogen to effect their conversions, a large hydrogen demand is still required even if these reactions are completed in liquid-phase systems. As a result, to maintain such a liquid-phase hydrotreating or hydrocracking reaction and still provide the needed levels of hydrogen, the diluent or solvent of these prior liquid-phase systems is required in order to provide a larger relative concentration of dissolved hydrogen as compared to unconverted oil to insure adequate conversions can occur in the liquid-phase hydrotreating and hydrocracking zones. See US Application Publication No. 2009/0095651. As such, larger and more complex liquid-phase systems are needed to achieve the desired conversions that still require large supplies of hydrogen.

Furthermore, there are distinct advantages to operating in a moving bed mode as opposed to a fixed bed mode. For example, fixed catalyst beds deactivate over time resulting in a declining level of performance. Moving beds, on the other hand, enable deactivated catalyst to be removed and fresh or regenerated catalyst to be added to the reactor to provide a continuous level of performance. Generally speaking, a moving bed operation requires less catalyst and less hydrocarbon inventory than a fixed bed operation of the same capacity, see U.S. Pat. No. 5,849,976.

Similarly, there are advantages to multiple moving bed reaction zones over a single moving bed process. Multiple reaction zone enable the liquid effluent to be mixed with additional hydrogen. Increasing the number of hydrogen mix points reduces the amount of liquid recycle. Lower liquid recycle reduces the capital and operating costs of the unit. Also, multiple reaction zone beds enable the liquid effluent from each reaction zone bed to be cooled. Increasing the number of cooling points can reduce the liquid recycle if the cooling achieved by mixing with hydrogen is not sufficient.

Although a wide variety of process flow schemes, operating conditions and catalysts have been used in commercial petroleum hydrocarbon conversion processes, there is always a demand for new methods and flow schemes that provide more useful products and improved product characteristics. In many cases, even minor variations in process flows or operating conditions can have significant effects on both quality and product selection. There generally is a need to balance economic considerations, such as capital expenditures and operational utility costs, with the desired quality of the produced products.

SUMMARY OF THE INVENTION

The systems and processes described herein relate to liquid phase hydrocarbon conversion processes using a solid catalyst in moving bed reactors. The moving bed reactors may be moving bed radial flow reactors. The moving bed radial flow reactors may contain an outer annulus and a centerpipe.

In one aspect a hydrocarbon conversion process for the conversion of at least one hydrocarbon to another hydrocarbon is provided that includes the steps of: providing a plurality of liquid phase moving bed reactors, transferring solid catalyst from the first reaction zone of the first moving bed reactor to the second reaction zone of the second moving bed reactor, passing a hydrocarbon feed stream to the first reactor that produces a first reactor effluent stream, passing the first reactor effluent stream to the second reactor. Optionally, portions of a second feed stream may be mixed with each of the reactor effluent streams and the mixture may be introduced to the next progressive reaction zone. The moving beds may be radial flow moving beds. The radial flow moving beds may contain an outer annulus and a centerpipe. In a second aspect, a hydrocarbon conversion process for the conversion of at least one hydrocarbon to another hydrocarbon is provided that includes the steps of: providing a plurality of liquid phase moving bed reactors configured in at least one vertical reactor stack having a top and a bottom, transferring solid catalyst from the first reaction zone of the first moving bed reactor to the second reaction zone of the second moving bed reactor through at least one catalyst transfer pipe, passing a hydrocarbon feed stream to the first reactor that produces a first reactor effluent stream, passing the first reactor effluent stream to the second reactor. Again, portions of a second feed stream may be mixed with each of the reactor effluent streams and the mixture may be introduced to the next progressive reaction zone. The moving beds may be radial flow moving beds.

In each aspect, the hydrocarbon feed stream can include one or more hydrocarbons, and an optional second feed stream can include another hydrocarbon or other reactant. Additionally, the plurality of liquid phase moving bed reactors can include a first moving bed reactor including a first outer annulus, a first centerpipe having a first centerpipe outlet, and a first reaction zone containing catalyst; and a second moving bed reactor including a second outer annulus, a second centerpipe having a first centerpipe outlet, and a second reaction zone containing catalyst. The first reactor feed stream can be received by the first outer annulus of the first moving bed reactor, can flow inward through the first reaction zone towards the first centerpipe, and can undergo a hydrocarbon conversion reaction in the first reaction zone to produce a first reactor effluent stream. The first reactor effluent stream can be removed from the first reactor through the first centerpipe outlet. The pressure of the of the first reactor effluent stream at the second reaction zone inlet is lower than the first reactor effluent stream when it is removed from the first centerpipe. Additionally, the pressure of the second reactor feed stream is lower than the first reactor effluent stream at the second reaction zone inlet. The second reactor feed stream can be received by the second reaction zone outer annulus, can flow inward through the second reaction zone towards the second centerpipe, and can undergo a hydrocarbon conversion reaction in the second reaction zone to produce a second reactor effluent stream. Finally, the second reactor effluent stream can be removed from the second reactor through the second centerpipe outlet.

BRIEF DESCRIPTION OF THE DRAWINGS

Specific examples have been chosen for purposes of illustration and description, and are shown in the accompanying drawings, forming a part of the specification.

DETAILED DESCRIPTION

Figure 1:
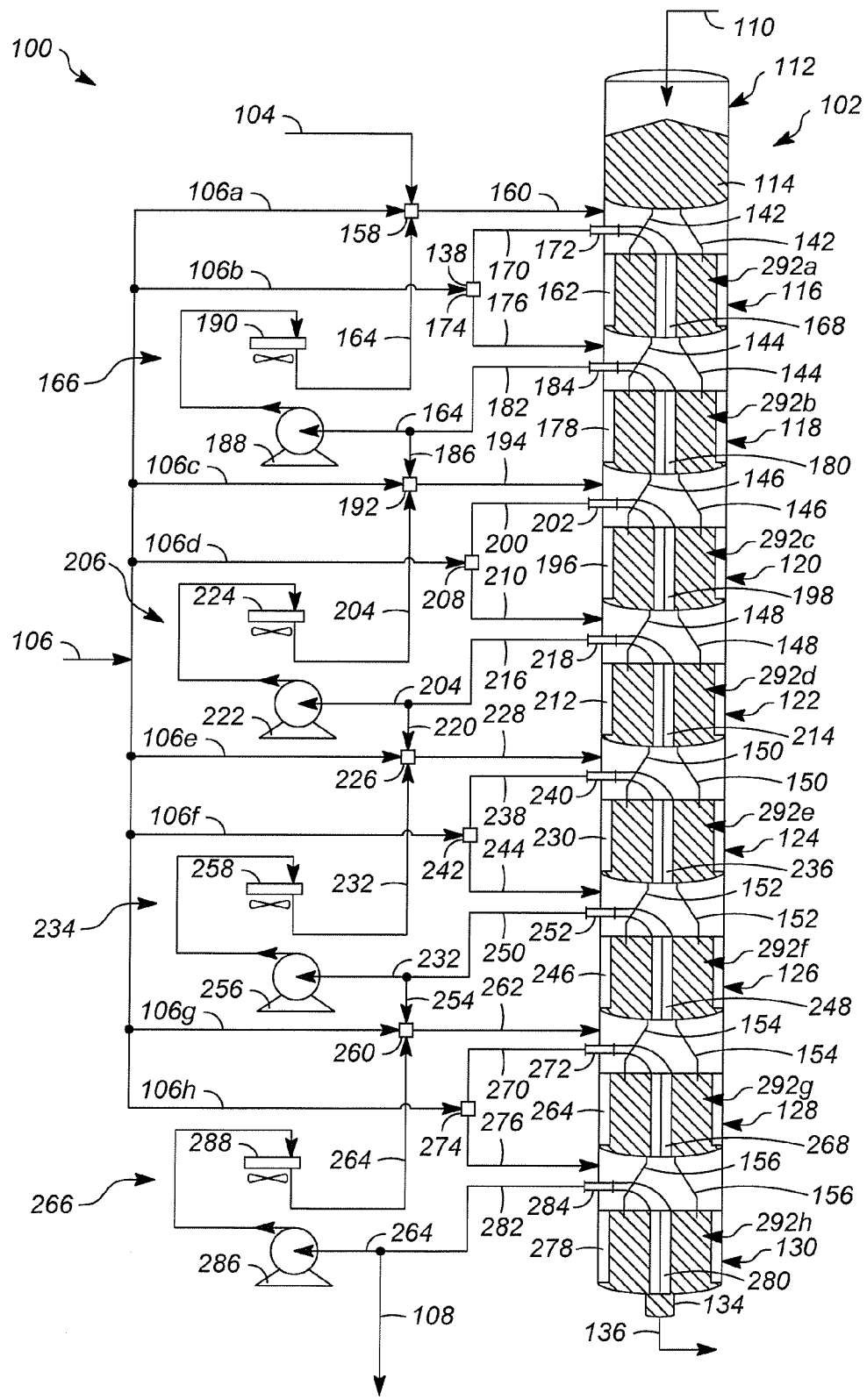
FIG. 1 illustrates one example of a hydrocarbon conversion process utilizing a single stack of reactors.

FIG. 1 illustrates one example of a hydrocarbon conversion system, illustrated generally at 100. Hydrocarbon conversion system 100 is a solid catalyst hydrocarbon conversion process operated in the liquid phase. Hydrocarbon conversion processes are well known in the art and include processes such as cracking, hydrocracking, alkylation of aromatics, alkylation of isoparaffins, isomerization, polymerization, reforming, dewaxing, hydrogenation, dehydrogenation, transalkylation, dealkylation, hydration, dehydration, hydrotreating, hydrodenitrogenation, hydrodesulfurization, and ring opening processes. Many of these processes are known to be successful when operated in the liquid phase mode.

An example of one class of liquid phase hydrocarbon conversion processes is olefin alkylation. In such an alkylation process, isobutene reacts with an acid site to form a tertiary carbenium ion ($tC_4^+$). The $tC_4^+$ ion reacts with an olefin molecule ($C_4=$) to form a larger tertiary carbenium ion ($tC_8^+$). The $tC_8^+$ ion undergoes hydride transfer with isobutane ($iC_4$), releasing an iso-octane (alkylate) molecule ($iC_8$) and reproducing the $tC_4^+$ ion.

Hydrocarbon conversion system 100 includes a plurality of moving bed radial flow reactors that are operated in the liquid phase mode. It is not necessary that the moving bed reactors be radial flow reactors, but for ease of understanding, the following description is directed to the embodiment where the moving beds are radial flow moving beds each having an outer annulus and a centerpipe. Each moving bed radial flow reactor can include a reaction zone in which the hydrocarbon conversion reaction occurs. The hydrocarbon conversion reaction any of the plurality of moving bed radial flow reactors can have a reaction temperature from about 10° C. to about 100° C.

The plurality of moving bed radial flow reactors can include from about four moving bed radial flow reactors to about thirty moving bed radial flow reactors. In one example, the plurality of moving bed radial flow reactors can be configured in at least one vertical reactor stack having a top and a bottom. In a second example, the plurality of moving bed radial flow reactors can be configured in at least a first vertical reactor stack and a second vertical reactor stack. The plurality of moving bed radial flow reactors can be configured in more than two vertical reactor stacks.

Figure 3:
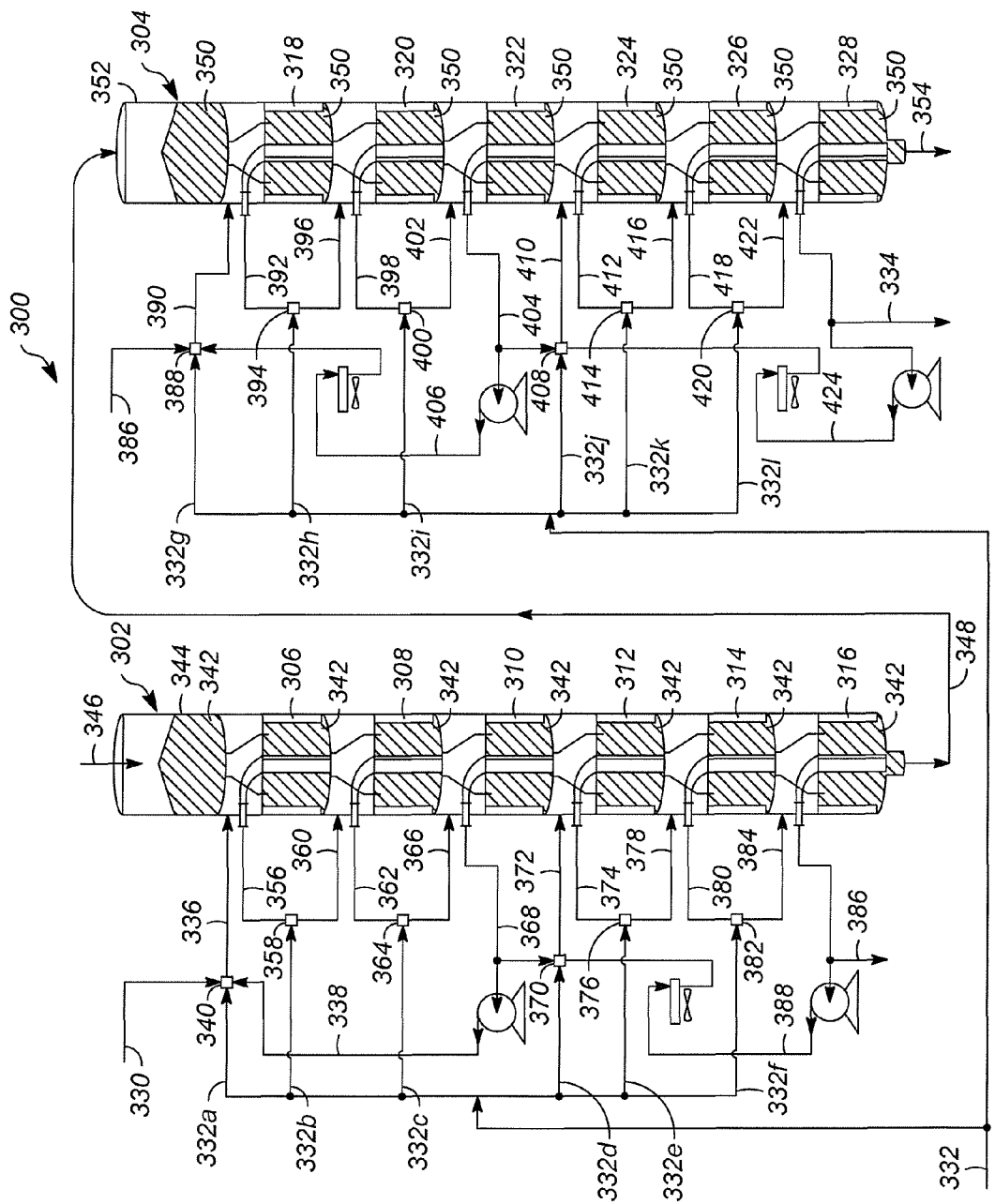
FIG. 3 illustrates one example of a hydrocarbon conversion process utilizing a double stack of reactors.

Some examples of hydrocarbon conversion reaction systems and processes described herein can include one reactor stack, or a plurality of reactor stacks. The moving beds may be radial flow reactors, or the flow may be cross flow, but not quite radial flow. For example, the flow may be inward, but also in the direction of gravity, such as from about 0 to about 30 degrees from the horizontal in the direction of gravity. In one example, a vertical reactor stack can include at least the four moving bed radial flow reactors. As illustrated in FIG. 1, vertical reactor stack 102 has eight moving bed radial flow reactors, including first moving bed radial flow reactor 116, second moving bed radial flow reactor 118, third moving bed radial flow reactor 120, fourth moving bed radial flow reactor 122, fifth moving bed radial flow reactor 124, sixth moving bed radial flow reactor 126, seventh moving bed radial flow reactor 128, and eighth moving bed radial flow reactor 130. As illustrated in FIG. 3, reaction system 300 includes a first vertical reactor stack 302 and a second vertical reactor stack 304. First vertical reactor stack 302 has six moving bed radial flow reactors, including first moving bed radial flow reactor 306, second moving bed radial flow reactor 308, third moving bed radial flow reactor 310, fourth moving bed radial flow reactor 312, fifth moving bed radial flow reactor 314, and sixth moving bed radial flow reactor 316. Second vertical reactor stack 304 also has six moving bed radial flow reactors, including first moving bed radial flow reactor 318, second moving bed radial flow reactor 320, third moving bed radial flow reactor 322, fourth moving bed radial flow reactor 324, fifth moving bed radial flow reactor 326, and sixth moving bed radial flow reactor 328. In a reaction system having two or more vertical reactor stacks, the vertical reactor stacks can have the same number of moving bed radial flow reactors, or different numbers of moving bed radial flow reactors.

Several applications of the process, such as alkylation and hydroprocessing, may involve a second feed stream and multiple injection points. The number of radial flow reactors to be used in an alkylation system, for example, can be determined by evaluating the benefit of an additional olefin injection point and the corresponding decrease in circulating liquid against the costs associated with adding an additional reactor. As reactors are added to a reactor stack, the stack increases in height, and it is preferred that reactor stacks be limited in height for practical considerations. Accordingly, it is preferred that two or more reactor stacks be utilized for alkylation reaction systems that include more than eight reactors. Although, it is recognized that two or more reactor stacks can be utilized for alkylation reaction systems that include eight reactors or less, and that it can be possible to utilize one reactor stack alkylation systems that include more than eight reactors. Similar determinations are made for other hydrocarbon conversion processes.

Referring back to FIGS. 1 and 2, a hydrocarbon feed stream 104 and a feed stream 106 can be provided through lines to the reactor stack 102 to produce an effluent product stream 108. The effluent product stream 108 can be in a liquid phase. For ease of understanding, the details of the invention will be explained with reference to one specific type of hydrocarbon conversion, alkylation, and where the moving beds are radial flow moving beds. In the case where the process is an alkylation process, the hydrocarbon feed stream can include an alkylation substrate, such as, for example, $C_3$-$C_5$ isoparaffins, and the second feed stream can include an alkylating agent, such as, for example, $C_3$-$C_5$ olefins. The alkylating agent feed stream is preferably divided into portions, and an alkylating agent injection point is preferably provided for each moving bed radial flow reactor in the reactor stack 102. The alkylation substrate and the alkylating agent can be provided to any of the moving bed radial flow reactors in a reactor feed stream, and the reactor feed stream can have a ratio of alkylation substrate to alkylating agent of from about 5:1 to about 15:1. The reactor feed streams can be in a liquid phase.

To promote the desired alkylation reaction, a catalyst stream 110 containing catalyst 114 can be provided the reaction zone of each moving bed radial flow reactor. Catalyst 114 can contain regenerated catalyst, fresh catalyst, or a combination of regenerated catalyst and fresh catalyst. As illustrated in FIG. 1, the vertical reactor stack 102 also includes a catalyst surge vessel 112 at the top of the vertical reactor stack 102 above the first moving bed radial flow reactor 116, and catalyst 114 can be provided to the catalyst surge vessel 112. Catalyst surge vessel 112 can then provide catalyst 114 to the reactors in the reactor stack 102.

The catalyst 114 can be transferred to each reactor of the reactor stack 102 via gravity. As catalyst 114 is provided to the catalyst surge vessel 112 in catalyst stream 110. The catalyst surge vessel can provide catalyst 114 to the first moving bed radial flow reactor 116 through at least one catalyst transfer pipe 142. As illustrated in FIG. 1, catalyst 114 can flow downwardly from the catalyst surge vessel 112 to the first reactor 116 through two catalyst transfer pipes 142.

Figure 2:
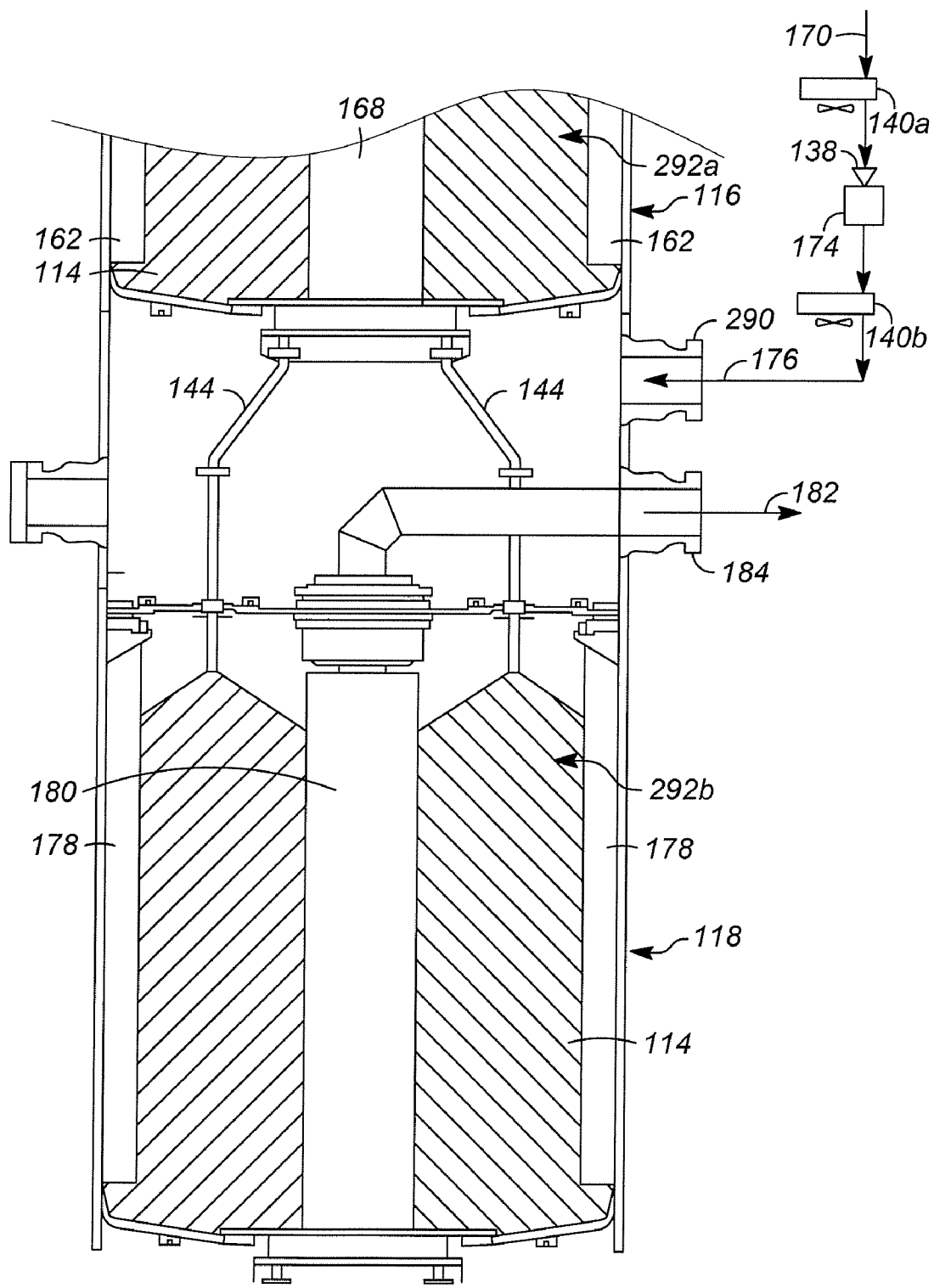
FIG. 2 illustrates a detail view of one reactor in the reactor stack of FIG. 1.

Referring to FIGS. 1 and 2, catalyst 114 can flow downwardly through the first reactor 116 via gravity, and can flow into the second reactor 118. For example, catalyst from the first reaction zone of the first moving bed radial flow reactor 116 can be transferred to the second reaction zone of the second moving bed radial flow reactor 118 through at least one catalyst transfer pipe 144. As illustrated in FIGS. 1 and 2, catalyst 114 can flow downwardly from the first reactor 116 to the second reactor 118 through two catalyst transfer pipes 144.

In the example illustrated in FIG. 1, there are at least two catalyst transfer pipes that transfer catalyst from each reactor to each subsequent reactor. In an alternative example, a single catalyst transfer pipe can be used to transfer catalyst from any one reactor to another reactor. The catalyst transfer pipes can be any suitable size. For example, catalyst transfer pipes can be sized to provide sufficient pressure drop for the mixers described below, while bypassing less than about 5% of the total reactor flow across the catalyst pipes.

As illustrated in FIGS. 1 and 2, catalyst 114 can be received by the second reactor 118 from the catalyst transfer pipes 144, and can flow downwardly through the second reactor 118 via gravity. Catalyst 114 can flow into the third reactor 120 via catalyst transfer pipes 146. Catalyst 114 can flow downwardly through the third reactor 120 via gravity, and can flow into the fourth reactor 122 through catalyst transfer pipes 148. Catalyst 114 can flow downwardly through the fourth reactor 122 via gravity, and can flow into the fifth reactor 124 through catalyst transfer pipes 150. Catalyst 114 can flow downwardly through the fifth reactor 124 via gravity, and can flow into the sixth reactor 126 through catalyst transfer pipes 152. Catalyst 114 can flow downwardly through the sixth reactor 126 via gravity, and can flow into the seventh reactor 128 through catalyst transfer pipes 154. Catalyst 114 can flow downwardly through the seventh reactor 128 via gravity, and can flow into the eighth reactor 130 through catalyst transfer pipes 156. In this manner, catalyst 114 flows via gravity through each reactor in the reactor stack 102.

Catalyst particles flow through the first reactor as a dense phase annular moving bed. At the outlet of first reactor, catalyst particles flow through catalyst transfer pipes before entering the second reactor. An aspect of the invention is the design of the catalyst transfer pipes. The catalyst transfer pipes are designed to transport the required flow of catalyst particles while minimizing the flow of process fluid. Process fluid that flows through the catalyst transfer pipes passes directly from the outlet of the upstream reactor to the next downstream reactor and bypassing the intended path of the process liquid through the unit operations between the upstream and downstream reactors.

It has been discovered that a key parameter in the design of the catalyst transfer pipes is the downward velocity of the liquid in the catalyst transfer pipes relative to the downward velocity of the catalyst particles. Low relative liquid velocities result in insufficient catalyst particle flow capacity of the catalyst transfer pipes. Also, low relative liquid velocities require increasing the catalyst transfer pipe length in order to develop the required liquid hydraulic resistance across the catalyst transfer pipe to balance the liquid hydraulic resistance through the unit operations between adjacent reactors.

High relative liquid velocities result in elevated liquid flow rates through the catalyst transfer pipes, which bypass the intended path of process liquid through the unit operations between adjacent reactors. High relative liquid velocities can also result in fluidization of the catalyst particles. Fluidization of the catalyst particles is very undesirable since it will likely lead to the breakage of catalyst particles. Fluidization of catalyst particles in the catalyst transfer pipes also dramatically reduces the liquid hydraulic resistance in the catalyst transfer pipes resulting in significantly higher liquid flow rates passing through the catalyst transfer pipes.

It has been found the range of relative liquid velocities in catalyst transfer pipes is typically required to be between 2 and 64 cm/s (0.07 and 2.1 feet per second) and the preferred range is between 3 and 79 cm/s (0.11 and 1.6 feet per second). In another embodiment the range of relative liquid velocities in catalyst transfer pipes may be between 1.5 and 123 cm/s (0.05 and 4.0 feet per second) and the preferred range between 3 and 76 cm/s (0.1 and 2.5 feet per second).

In each reactor in reactor stack 102, the catalyst can be utilized to react at least a portion of the hydrocarbon feed stream and at least a portion of the alkylating agent feed stream to produce alkylate effluent. As catalyst 114 is utilized in each of the reactors in the reactor stack 102, it can become deactivated. Deactivated catalyst can be removed from the bottom of the vertical reactor stack 102 in a deactivated catalyst stream 136 via an outlet 134, and a deactivated catalyst stream 136 can be provided to a catalyst regenerator (not shown), which can be a continuous catalyst regenerator, and the deactivated catalyst can be regenerated to produce regenerated catalyst. The regenerated catalyst can be provided back to top of the vertical reactor stack 102. As illustrated in FIG. 1, regenerated catalyst can be provided to the catalyst surge vessel 112 in catalyst stream 110.

Referring to FIG. 1, as described above, the alkylating agent feed stream 106 can be divided into one or more portions, such as first alkylating agent feed stream portion 106a, second alkylating agent feed stream portion 106b, third alkylating feed stream portion 106c, fourth alkylating agent feed stream portion 106d, fifth alkylating agent feed stream portion 106e, sixth alkylating agent feed stream portion 106f, seventh alkylating agent feed stream portion 106g, and eighth alkylating agent feed stream portion 106h.

The hydrocarbon feed stream 104 for the alkylation reaction can be provided to a first mixer 158, where it can be combined with first alkylating agent feed stream portion 106a. As illustrated, the mixers are external to the moving bed radial flow reactors. It should be understood, however, that the mixers described herein could alternatively be internal to the moving bed radial flow reactors. First reactor feed stream 160 can be provided from the first mixer 158, and can be injected into an outer annulus 162 of the first reactor 116. First reactor feed stream 160 can be in a liquid phase, and can contain the hydrocarbon feed stream 104 and the first alkylating agent feed stream portion 106a. First reactor feed stream 160 can also contain a circulation stream 164 of the reactor effluent from the second reactor 118, which can be provided to the first mixer 158 by first circulation loop 166. In an alternative embodiment, a circulation stream can be separated from a reactor effluent stream from another moving bed radial flow reactor downstream of the second moving bed radial flow reactor, and can be provided to the first mixer.

The first moving bed radial flow reactor 116 can include a first outer annulus 162, a first centerpipe 168 having a first centerpipe outlet 172, and a first reaction zone 292a containing catalyst. First reactor feed stream 160 can flow radially inward from the outer annulus 162 of the first reactor 116 towards the first centerpipe 168 of the first reactor 116. As the first reactor feed stream 160 flows radially inward through the first reactor 116, it passes through catalyst 114 in the first reaction zone 292a and can undergo alkylation to produce a first reactor effluent stream 170 that can be removed from the first reactor 116 via a first centerpipe outlet 172. First reactor effluent stream 170 can be in a liquid phase.

First reactor effluent stream 170 can be provided to second mixer 174 through the second mixer inlet 138, where it can be mixed with second alkylating agent feed stream portion 106b to form second reactor feed stream 176. The first reactor effluent stream 170 can have a pressure at the second mixer inlet 138 that is lower than a pressure of the first reactor effluent stream 170 when it is removed from the first reactor 116 through the first centerpipe outlet 172. Additionally, the second reactor feed stream 176 can have a pressure that is lower than the pressure of the first reactor effluent stream 172 at the second mixer inlet 138. The pressures of each subsequent reactor effluent stream and reactor feed stream can be designed in a similar manner. Such design of the pressures can facilitate flow of the of the reactor effluent streams and the reactor feed streams within the alkylation system 100 without requiring a pump or raise in pressure to provide a reactor effluent stream to a mixer, and then provide a reactor feed stream from a mixer to the next reactor. A system design that does not require pumping of the reactor effluent streams or reactor feed streams can provide a reduction in the capital and operation costs associated with adding olefin injection points and increasing the internal i/o ratio of the reactors.

As illustrated in FIG. 2, the alkylation system can include cooling a reactor effluent stream or a reactor feed stream to remove heat generated during the exothermic alkylation reaction. For example, the alkylation system can include cooling the first reactor effluent stream 170 or second reactor feed stream 176 in a cooling exchanger. In one example, the first reactor effluent stream 170 can be passed to a cooling exchanger 140a, to be cooled prior to being passed to the inlet 138 of the second mixer 174. In another example, the second reactor feed stream 176 can be passed from the second mixer 174 to a cooling exchanger 140b. In an alkylation system where the pressure of the first reactor effluent is lower at the second mixer inlet 138 that at the first centerpipe outlet 172, and the pressure of the second reactor feed stream 176 is lower than the pressure of the first reactor effluent stream 170 at the second mixer inlet 138, the step of cooling the first reactor effluent stream 170 or the second reactor feed stream 176 can be accomplished without requiring a raise in pressure or pumping.

Referring to FIGS. 1 and 2, the second moving bed radial flow reactor 118 can include a second outer annulus 178, a second centerpipe 180 having a second centerpipe outlet 184, and a second reaction zone 292b containing catalyst. Second reactor feed stream 176 can be injected through a second reactor inlet 290 into the outer annulus 178 of the second reactor 118. As the second reactor feed stream 176 flows radially inward through the second reactor 118 to the second reactor centerpipe 180, it passes through catalyst 114 in the second reaction zone 292b and can undergo alkylation to produce a second reactor effluent stream 182, which can be in a liquid phase, and can be removed from the second reactor 118 via a second centerpipe outlet 184.

As illustrated in FIG. 1, second reactor effluent stream 182 can be divided into at least two portions, including circulation stream 164 and reaction portion 186. Circulation stream 164 can be separated from the second reactor effluent stream 182, and can be provided to the first mixer through the first circulation loop 166. First circulation loop 166 can include at least one pump 188. First circulation loop 166 can also include at least one cooling exchanger 190, which can cool the circulation stream 164 prior to providing the circulation stream to the first mixer in order to remove heat generated during the alkylation reaction. Reaction portion 186 of the second reactor effluent stream 182 can be provided to third mixer 192, where it can be combined with third alkylating agent feed stream portion 106c.

The third moving bed radial flow reactor 120 can include a third outer annulus 196, a third centerpipe 198 having a third centerpipe outlet 202, and a third reaction zone 292c containing catalyst. The third reactor feed stream 194 can be provided from the third mixer 192, and can be injected into an outer annulus 196 of the third reactor 120. Third reactor feed stream 194 can contain the reaction portion 186 of second reactor effluent stream 182 and third alkylating agent feed stream portion 106c. Third reactor feed stream 194 can also contain a circulation stream 204 of the alkylate effluent from the fourth reactor 122, which can be provided to the third mixer 192 by second circulation loop 206.

Third reactor feed stream 194 can flow radially inward from the outer annulus 196 of the third reactor 120 to the third centerpipe 198 of the third reactor 120. As the third reactor feed stream 194 flows radially inward through the third reactor 120, it passes through catalyst 114 in the third reaction zone 292c and can undergo alkylation to produce a third reactor effluent stream 120 that can be removed from the third reactor 120 via a third centerpipe outlet 202. Third reactor effluent stream 200, which can be in a liquid phase, can be provided to fourth mixer 208, where it can be mixed with fourth alkylating agent feed stream portion 106d to form fourth reactor feed stream 210.

The fourth moving bed radial flow reactor 122 can include a fourth outer annulus 212, a fourth centerpipe 214 having a fourth centerpipe outlet 218, and a fourth reaction zone 292d containing catalyst. Fourth reactor feed stream 210 can be injected into the outer annulus 212f the fourth reactor 122. Fourth reactor feed stream 210 can flow radially inward from the outer annulus 212 of the fourth reactor 122 to the fourth centerpipe 214 of the fourth reactor 122. As the fourth reactor feed stream 210 flows radially inward through the fourth reactor 122, it passes through catalyst 114 in the fourth reaction zone 292d and can undergo alkylation to produce a fourth reactor effluent stream 216, which can be in a liquid phase, and can be removed from the fourth reactor 122 via a fourth centerpipe outlet 218.

Fourth reactor effluent stream 216 can be divided into at least two portions, including circulation stream 204 and reaction portion 220. Circulation stream 204 of the fourth reactor effluent stream 216 can be provided to second circulation loop 206. Second circulation loop 206 can include at least one pump 222. Second circulation loop 206 can also include at least one cooling exchanger 224, which can cool the circulation stream 204 of the fourth reactor effluent stream 216 to remove heat generated during the alkylation reaction to remove heat generated during the alkylation reaction. Reaction portion 220 of the fourth reactor effluent stream 216 can be provided to fifth mixer 226, where it can be combined with fifth alkylating agent feed stream portion 106e.

The fifth moving bed radial flow reactor 124 can include a fifth outer annulus 230, a fifth centerpipe 236 having a fifth centerpipe outlet 240, and a fifth reaction zone 292e containing catalyst. Fifth reactor feed stream 228 can be provided from the fifth mixer 226, and can be injected into an outer annulus 230 of the fifth reactor 124. Fifth reactor feed stream 228 can contain the reaction portion 220 of fourth reactor effluent stream 216 and fifth alkylating agent feed stream portion 106e. Fifth reactor feed stream 228 can also contain a circulation stream 232 of the alkylate effluent from the sixth reactor 126, which can be provided to the fifth mixer 226 by third circulation loop 234.

Fifth reactor feed stream 228 can flow radially inward from the outer annulus 230 of the fifth reactor 124 to the fifth centerpipe 236 of the fifth reactor 124. As the fifth reactor feed stream 228 flows radially inward through the fifth reactor 124, it passes through catalyst 114 in the fifth reaction zone 292e and can undergo alkylation to produce a fifth reactor effluent stream 238 that can be removed from the fifth reactor 124 via a fifth centerpipe outlet 240. Fifth reactor effluent stream 238, which can be in a liquid phase, can be provided to sixth mixer 242, where it can be mixed with sixth alkylating agent feed stream portion 106f to form sixth reactor feed stream 244.

The sixth moving bed radial flow reactor 126 can include a sixth outer annulus 246, a sixth centerpipe 248 having a sixth centerpipe outlet 252, and a sixth reaction zone 292f containing catalyst. Sixth reactor feed stream 244 can be injected into the outer annulus 246 of the sixth reactor 126. Sixth reactor feed stream 244 can flow radially inward from the outer annulus 246 of the sixth reactor 126 to the sixth centerpipe 248 of the sixth reactor 126. As the sixth reactor feed stream 244 flows radially inward through the sixth reactor 126, it passes through catalyst 114 in the sixth reaction zone 292f and can undergo alkylation to produce a sixth reactor effluent stream 250, which can be in a liquid phase, and can be removed from the sixth reactor 126 via a sixth centerpipe outlet 252.

Sixth reactor effluent stream 250 can be divided into at least two portions, including circulation stream 232 and reaction portion 254. Circulation stream 232 of the sixth reactor effluent stream 250 can be provided to third circulation loop 234. Third circulation loop 234 can include at least one pump 256. Third circulation loop 234 can also include at least one cooling exchanger 258, which can cool the circulation stream 232 of the sixth reactor effluent stream 250 to remove heat generated during the alkylation reaction. Reaction portion 254 of the sixth reactor effluent stream 250 can be provided to seventh mixer 260, where it can be combined with seventh alkylating agent feed stream portion 106g.

The seventh moving bed radial flow reactor 128 can include a seventh outer annulus 264, a seventh centerpipe 268 having a seventh centerpipe outlet 272, and a seventh reaction zone 292g containing catalyst. Seventh reactor feed stream 262 can be provided from the seventh mixer 260, and can be injected into an outer annulus 264 of the seventh reactor 128. Seventh reactor feed stream 262 can contain the reaction portion 254 of sixth reactor effluent stream 250 and seventh alkylating agent feed stream portion 106g. Seventh reactor feed stream 262 can also contain a circulation stream 264 of the alkylate effluent from the eighth reactor 130, which can be provided to the seventh mixer 260 by fourth circulation loop 266.

Seventh reactor feed stream 262 can flow radially inward from the outer annulus 264 of the seventh reactor 128 to the seventh centerpipe 266 of the seventh reactor 128. As the seventh reactor feed stream 262 flows radially inward through the seventh reactor 128, it passes through catalyst 114 in the seventh reaction zone 292g and can undergo alkylation to produce a seventh reactor effluent stream 270 that can be removed from the seventh reactor 128 via a seventh centerpipe outlet 272. Seventh reactor effluent stream 272, which can be in a liquid phase, can be provided to eighth mixer 274, where it can be mixed with eighth alkylating agent feed stream portion 106h to form eighth reactor feed stream 276.

The eighth moving bed radial flow reactor 130 can include a eighth outer annulus 278, a eighth centerpipe 280 having a eighth centerpipe outlet 284, and a eighth reaction zone 292h containing catalyst. Eighth reactor feed stream 276 can be injected into the outer annulus 278 of the eighth reactor 130. Eighth reactor feed stream 276 can flow radially inward from the outer annulus 278 of the eighth reactor 130 to the eighth centerpipe 280 of the eighth reactor 130. As the eighth reactor feed stream 276 flows radially inward through the eighth reactor 130, it passes through catalyst 114 in the eighth reaction zone 292h and can undergo alkylation to produce a eighth reactor effluent stream 282 that can be removed from the eighth reactor 130 via a eighth centerpipe outlet 284.

The eighth reactor effluent stream 282 can be divided. A recirculation stream 264 of the eighth reactor effluent stream 282 can be provided to the fourth circulation loop 266. Fourth circulation loop 266 can include at least one pump 286. Fourth circulation loop 266 can also include at least one cooling exchanger 288, which can cool the circulation stream 264 of the eighth reactor effluent stream 282 to remove heat generated during the alkylation reaction. The remaining portion of eighth reactor effluent stream 282 can be removed from the alkylation system 100 as alkylate effluent product stream 108. In at least one example, the alkylate effluent product stream 108 can be provided to a downstream unit, such as an isostripper, for further processing.

FIG. 3 illustrates an alkylation system 300 that includes a first vertical reactor stack 302 and a second vertical reactor stack 304. As discussed above, the first vertical reactor stack 302 and the second vertical reactor stack each include six moving bed radial flow reactors. The alkylation system 300 can function in a similar manner to alkylation system 100 with respect to the structure of the moving bed radial flow reactors, and the flow scheme of the reactor feed streams and reactor effluent streams.

A hydrocarbon feed stream 330 and an alkylating agent feed stream 332 can be provided through lines to the first reactor stack 302, and the alkylation system 300 can produce an alkylate effluent product stream 334. The alkylating agent feed stream is preferably divided into portions, and an alkylating agent injection point is preferably provided for each moving bed radial flow reactor in the first reactor stack 302 and the second reactor stack 304. As illustrated in FIG. 3, the alkylating agent feed stream is divided into twelve portions, 332a through 332l, and each portion of the alkylating agent feed stream is provided to a mixer that provides a reactor feed stream to one of the moving bed radial flow reactors.

As illustrated in FIG. 3, the hydrocarbon feed stream 330 and the first alkylating agent feed stream portion 332a are provided to a first mixer 340. A circulation stream 338 can be separated from the reactor effluent stream of a reactor downstream of the first reactor 306, and can also be provided to the first mixer 340. First mixer 340 can provide a first reactor feed stream 336 to the first moving bed radial flow reactor 306.

Catalyst 342 can be provided to the first reactor 306 from a catalyst surge vessel 344 that receives a catalyst stream 346. The catalyst stream 346 can contain fresh catalyst, regenerated catalyst, or a combination of fresh and regenerated catalyst. The catalyst 342 can flow downward through a reaction zone in each reactor in the first vertical reactor stack 302, and can participate in the alkylation reaction occurring in each reaction zone. Catalyst can be removed from the first reactor stack 302 in a first reactor stack catalyst stream 348. Catalyst 350 from the first reactor stack catalyst stream 348 can be provided to a second catalyst surge vessel 352 at the top of the second vertical reactor stack 304. In one example, fresh or regenerated catalyst can also be provided to the second catalyst surge vessel 352, or at least a portion of the catalyst in the first reactor stack catalyst stream 348 can be regenerated prior to being provided to the second catalyst surge vessel 352. Catalyst 350 can flow downward through a reaction zone in each reactor in the second vertical reactor stack 304, and can participate in the alkylation reaction occurring in each reaction zone. A deactivated catalyst stream 354 can be removed from the bottom of the second vertical reactor stack 304.

The first reactor feed stream 336 can undergo an alkylation reaction in the reaction zone of the first moving bed radial flow reactor 306, and a first reactor effluent stream can be removed from the first moving bed radial flow reactor 306. The first reactor effluent stream and the second alkylating agent feed stream portion 332b can be provided to a second mixer 358 that provides a second reactor feed stream 360 to the second reactor 308.

The alkylation system 300, like the alkylation system 100 discussed above, can be designed so that the pressure of the first reactor effluent stream is lower at the second mixer inlet than the pressure when it is removed from the first reactor, and so that the pressure of the second reactor feed stream is lower than the pressure of the first reactor effluent stream at the second mixer inlet. The pressures of each subsequent reactor effluent stream and reactor feed stream can be similarly designed.

The second reactor feed stream 360 can undergo an alkylation reaction in the reaction zone of the second moving bed radial flow reactor 308, and a second reactor effluent stream 362 can be removed from the second moving bed radial flow reactor 308. The second reactor effluent stream and the third alkylating agent feed stream portion 332c can be provided to a third mixer 364 that provides a third reactor feed stream 366 to the second reactor 310.

The third reactor feed stream 366 can undergo an alkylation reaction in the reaction zone of the third moving bed radial flow reactor 310, and a third reactor effluent stream 368 can be removed from the third moving bed radial flow reactor 310. A circulation stream 338 can be separated from the third reactor effluent stream 368, and the remainder can be provided, along with the fourth alkylating agent feed stream portion 332d to a fourth mixer 370 that provides a fourth reactor feed stream 372 to the fourth reactor 312.

The fourth reactor feed stream 372 can undergo an alkylation reaction in the reaction zone of the fourth moving bed radial flow reactor 312, and a fourth reactor effluent stream 374 can be removed from the fourth moving bed radial flow reactor 312. The fourth reactor effluent stream and the fifth alkylating agent feed stream portion 332e can be provided to a fifth mixer 376 that provides a fifth reactor feed stream 378 to the fifth reactor 314.

The fifth reactor feed stream 378 can undergo an alkylation reaction in the reaction zone of the fifth moving bed radial flow reactor 314, and a fifth reactor effluent stream 380 can be removed from the fifth moving bed radial flow reactor 314. The fifth reactor effluent stream 380 and the sixth alkylating agent feed stream portion 332f can be provided to a sixth mixer 382 that provides a sixth reactor feed stream 384 to the sixth reactor 316, which is the bottom reactor in the first vertical reactor stack 302.

A sixth reactor effluent stream 386 can be removed from the sixth reactor 316. A circulation stream 388 can be separated from the sixth reactor effluent stream 386 and can be passed to an upstream mixer, such as fourth mixer 370, where it can be mixed into a reactor feed stream. At least a portion of the remainder of the sixth reactor effluent stream 386 can be passed to the top of the second vertical reactor stack 304 to undergo further alkylation.

As illustrated in FIG. 3, sixth reactor effluent stream 386 and seventh alkylating agent feed stream portion 332g can be provided to a seventh mixer 388 that provides a seventh reactor feed stream 390 to the first reactor 318 of the second vertical reactor stack 304.

The seventh reactor feed stream 390 can undergo an alkylation reaction in the reaction zone of the first moving bed radial flow reactor 318 of the second vertical reactor stack 304, and a seventh reactor effluent stream 392 can be removed from the first moving bed radial flow reactor 318 of the second vertical reactor stack 304. The seventh reactor effluent stream 392 and the eighth alkylating agent feed stream portion 332h can be provided to a eighth mixer 394 that provides a eighth reactor feed stream 396 to the second moving bed radial flow reactor 320 of the second vertical reactor stack 304.

The eighth reactor feed stream 396 can undergo an alkylation reaction in the reaction zone of the second moving bed radial flow reactor 320 of the second vertical reactor stack 304, and an eighth reactor effluent stream 398 can be removed from the second moving bed radial flow reactor 320 of the second vertical reactor stack 304. The eighth reactor effluent stream 398 and the ninth alkylating agent feed stream portion 332i can be provided to a ninth mixer 400 that provides a ninth reactor feed stream 402 to the third moving bed radial flow reactor 322 of the second vertical reactor stack 304.

The ninth reactor feed stream 403 can undergo an alkylation reaction in the reaction zone of the third moving bed radial flow reactor 322 of the second vertical reactor stack 304, and a ninth reactor effluent stream 404 can be removed from the third moving bed radial flow reactor 322 of the second vertical reactor stack 304. A circulation stream 406 can be separated from the ninth reactor effluent stream 404 and can be provided to an upstream mixer to be combined into a reactor feed stream. The remainder of the ninth reactor effluent stream 404 and the tenth alkylating agent feed stream portion 332j can be provided to a tenth mixer 408 that provides a tenth reactor feed stream 410 to the fourth moving bed radial flow reactor 324 of the second vertical reactor stack 304.

The tenth reactor feed stream 410 can undergo an alkylation reaction in the reaction zone of the fourth moving bed radial flow reactor 324 of the second vertical reactor stack 304, and a tenth reactor effluent stream 412 can be removed from the fourth moving bed radial flow reactor 324 of the second vertical reactor stack 304. The tenth reactor effluent stream 412 and the eleventh alkylating agent feed stream portion 332k can be provided to an eleventh mixer 414 that provides an eleventh reactor feed stream 416 to the fifth moving bed radial flow reactor 326 of the second vertical reactor stack 304.

The eleventh reactor feed stream 416 can undergo an alkylation reaction in the reaction zone of the fifth moving bed radial flow reactor 326 of the second vertical reactor stack 304, and an eleventh reactor effluent stream 418 can be removed from the fifth moving bed radial flow reactor 326 of the second vertical reactor stack 304. The eleventh reactor effluent stream 418 and the twelfth alkylating agent feed stream portion 332l can be provided to a twelfth mixer 420 that provides an twelfth reactor feed stream 422 to the sixth moving bed radial flow reactor 328, which is the bottom reactor of the of the second vertical reactor stack 304.

The twelfth reactor feed stream 422 can undergo an alkylation reaction in the reaction zone of the sixth moving bed radial flow reactor 328 of the second vertical reactor stack 304, and the alkylate effluent product stream 334 can be removed from the sixth moving bed radial flow reactor 328 of the second vertical reactor stack 304. A circulation stream 424 can be separated from the alkylate effluent product stream 334, and can be provided to an upstream mixer to be combined into a reactor feed stream.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

It must be emphasized that the above description is merely illustrative of a one embodiment of the invention and is not intended as an undue limitation on the generally broad scope of the invention. Moreover, while the detailed description is narrow in scope and focuses on alkylation, one skilled in the art will understand how to extrapolate to the broader scope of the invention such as the application of the invention to additional hydrocarbon conversion reactions.

The invention claimed is:

1. A liquid phase hydrocarbon conversion process comprising the steps of:
   providing a plurality of moving bed reactors including:
   a first moving bed reactor including a first reaction zone containing catalyst; and
   a second moving bed reactor including a second reaction zone containing catalyst;
   transferring catalyst from the first reaction zone of the first moving bed reactor to the second reaction zone of the second moving bed reactor;
   passing a liquid phase hydrocarbon feed stream to the first reactor, wherein the hydrocarbon feed stream flows through the first reaction zone and undergoes a hydrocarbon conversion reaction in the first reaction zone to produce a first reactor effluent stream;
   passing the first reactor effluent stream to the second reactor, the first reactor effluent stream having a pressure at the inlet to the second reactor that is lower than the pressure of the first reactor effluent stream at the outlet of the first reactor, wherein the first reactor effluent stream flows through the second reaction zone and undergoes a hydrocarbon conversion reaction in the second reaction zone to produce a second reactor effluent stream; and
   removing the second reactor effluent stream from the second reactor.

2. The hydrocarbon conversion process of claim 1, wherein the liquid phase flow is primary radially or horizontally through the moving beds.

3. The hydrocarbon conversion process of claim 1, wherein the step of transferring catalyst comprises transferring catalyst from the first reaction zone of the first moving bed reactor to the second reaction zone of the second moving bed reactor through at least one catalyst transfer pipe.

4. The hydrocarbon conversion process of claim 1, wherein the plurality of moving bed reactors are configured in at least one vertical reactor stack having a top and a bottom, the vertical reactor stack comprising at least four moving bed reactors.

5. The hydrocarbon conversion process of claim 4, further comprising the steps of:

removing catalyst from the bottom of the vertical reactor stack in a deactivated catalyst stream;

regenerating the deactivated catalyst to produce regenerated catalyst; and providing the regenerated catalyst to the top of the vertical reactor stack.

6. The hydrocarbon conversion process of claim 5, the vertical reactor stack further comprising a catalyst surge vessel at the top of the vertical reactor stack above the first reactor, wherein the regenerated catalyst is provided to the catalyst surge vessel, and the catalyst surge vessel provides catalyst to the first moving bed reactor through at least one catalyst transfer pipe.

7. The hydrocarbon conversion process of claim 1, wherein the plurality of moving bed reactors comprises from about four moving bed radial flow reactors to about thirty moving bed radial flow reactors.

8. The hydrocarbon conversion process of claim 1 wherein the liquid phase flow is primary downward through the moving beds.

9. The hydrocarbon conversion process of claim 1, further comprising the step of cooling the first reactor effluent stream or second reactor feed stream in a cooling exchanger.

10. The hydrocarbon conversion process of claim 1, the process further comprising separating a circulation stream from the second reactor effluent stream or wherein the process further comprises additional moving bed reactors downstream of the second reactor, separating the circulation stream from a reactor effluent stream of an additional moving bed reactor downstream of the second moving bed reactor; and providing the circulation stream to one or more reactors.

11. The hydrocarbon conversion process of claim 10, further comprising cooling the circulation stream in a cooling exchanger prior to providing the circulation stream to one or more reactors.

12. The hydrocarbon conversion process of claim 1, wherein the hydrocarbon conversion reaction in at least one of the moving bed reactors has a reaction temperature from about 10° C. to about 100° C.

13. The hydrocarbon conversion process of claim 1, wherein the reactor feed streams and the reactor effluent streams are in a liquid phase.

14. The process of claim 1 wherein the catalyst is transferred from the first reaction zone of the first moving bed reactor to the second reaction zone of the second moving bed reactor through at least one catalyst transfer pipe while the catalyst is submerged in a liquid portion of the first reactor effluent stream; and wherein the relative velocity of the liquid portion in the catalyst transfer pipe to the catalyst in the catalyst transfer pipe ranges from about 1.5 to about 123 cm/s (about 0.05 to about 4.0 feet per second).

15. The process of claim 1:
wherein the a plurality of moving bed reactors are configured in at least one vertical reactor stack having a top and a bottom
wherein the first moving bed reactor further comprises a first outer annulus and a first centerpipe having a first centerpipe outlet,
wherein the second moving bed reactor further comprises a second outer annulus and a second centerpipe having a second centerpipe outlet,
wherein the transferring of catalyst from the first reaction zone to the second reaction zone is through at least one catalyst transfer pipe;

further comprising generating the first reactor feed stream by passing a liquid phase hydrocarbon feed stream including a first portion of a second feed stream to a first mixer that produces a first reactor feed stream;

wherein the passing of the first reactor feed stream to the first reactor further comprises receiving the first reactor feed stream by the first outer annulus, flowing the first reactor feed stream radially inward through the first reaction zone towards the first centerpipe and the first reactor effluent stream is removed from the first reactor through the first centerpipe outlet at a first pressure;

further comprising passing first reactor effluent stream and a second portion of the second feed stream to a second mixer, the first reactor effluent stream having a second pressure at the second mixer that is lower than the first pressure of the first reactor effluent stream when it is removed from the first centerpipe;

wherein the passing of the first reactor effluent to the second reactor further comprises the second reactor feed stream having a pressure that is lower than the second pressure of the first reactor effluent stream at the second mixer, receiving the second reactor feed stream by the second outer annulus, flowing the second reactor feed stream radially inward through the second reaction zone towards the second centerpipe and and wherein the removing of the second reactor effluent stream is through the second centerpipe outlet.

16. The hydrocarbon conversion process of claim 15, wherein the hydrocarbon conversion process is an alkylation process, the hydrocarbon feed stream comprises $C_3$-$C_5$ isoparaffins, and the alkylating agent in the alkylating agent feed stream comprises $C_3$-$C_5$ olefins.

17. The hydrocarbon conversion process of claim 15, further comprising the steps of:
removing catalyst from the bottom of the vertical reactor stack in a deactivated catalyst stream;
regenerating the deactivated catalyst to produce regenerated catalyst; and
providing the regenerated catalyst to the top of the vertical reactor stack.

18. The hydrocarbon conversion process of claim 15, wherein the reactor feed streams flow radially outward from the centerpipe to the outer annulus.

19. The hydrocarbon conversion process of claim 15, wherein the plurality of moving bed reactors comprises from about four moving bed reactors to about thirty moving bed reactors.

20. The hydrocarbon conversion process of claim 15, the process further comprising the steps of:
separating a circulation stream from the second reactor effluent stream or from a reactor effluent stream from another moving bed reactor downstream of the second moving bed reactor; and
providing the circulation stream to the first mixer, wherein the first reactor feed stream includes the hydrocarbon feed stream, the first portion of the second feed stream, and the circulation stream.

21. The hydrocarbon conversion process of claim 15 wherein the catalyst in the at least one catalyst transfer pipe is submerged in a liquid portion of the first reactor effluent stream; and wherein the relative velocity of the liquid portion in the catalyst transfer pipe to the catalyst in the catalyst transfer pipe ranges from about 1.5 to about 123 cm/s (about 0.05 to about 4.0 feet per second).

* * * * *